(12) United States Patent
Scivoletto (10) Patent No.: US 10,307,230 B2
(45) Date of Patent: Jun. 4, 2019

(54) DENTURE-SECURING DEVICE

(71) Applicant: Bondezz LLC, Fort Lauderdale, FL (US)

(72) Inventor: Joseph C. Scivoletto, Margate, FL (US)

(73) Assignee: Bondezz Corp, Boca Raton, FL (US)

( * ) Notice: Subject to any disclaimer, the term of this patent is extended or adjusted under 35 U.S.C. 154(b) by 0 days.

(21) Appl. No.: 15/457,452

(22) Filed: Mar. 13, 2017

(65) Prior Publication Data

US 2019/0105136 A1     Apr. 11, 2019

(51) Int. Cl.
| | | |
|---|---|---|
| *A61C 13/00* | (2006.01) |
| *A61C 13/24* | (2006.01) |
| *A61C 19/06* | (2006.01) |
| *A61C 13/07* | (2006.01) |

(52) U.S. Cl.
CPC ........ *A61C 13/245* (2013.01); *A61C 13/0025* (2013.01); *A61C 19/063* (2013.01)

(58) Field of Classification Search
CPC .................................................. A61C 13/0025
USPC ........................................................ 433/168.1
See application file for complete search history.

(56) References Cited

U.S. PATENT DOCUMENTS

| | | | | |
|---|---|---|---|---|
| 1,050,561 A | * | 1/1913 | Moore | A61C 13/0025 433/168.1 |
| 2,392,513 A | * | 1/1946 | Town | A61C 13/0025 433/168.1 |
| 2,628,425 A | * | 2/1953 | Rosner, Jr. | A61C 13/0025 433/168.1 |
| 2,664,631 A | * | 1/1954 | Hollander | A61K 6/083 433/168.1 |
| 3,226,826 A | * | 1/1966 | Town | A61C 13/0025 428/91 |
| 5,431,563 A | * | 7/1995 | Huybrechts | A42B 3/12 128/862 |
| 7,195,484 B1 | * | 3/2007 | Wagner | A61C 13/0025 433/168.1 |
| 2010/0248183 A1 | * | 9/2010 | Tudek | A61C 13/0025 433/168.1 |

FOREIGN PATENT DOCUMENTS

| | | | |
|---|---|---|---|
| DE | 1566252 | * | 11/1970 |
| FR | 2641965 | * | 7/1990 |

* cited by examiner

*Primary Examiner* — Ralph A Lewis
(74) *Attorney, Agent, or Firm* — H. John Rizvi; John Rizvi, P.A.

(57) ABSTRACT

A denture-securing device is provided that is usable to substantially secure a denture within a mouth. The denture-securing device may be used with top dentures, bottom dentures, or other configurations of dentures. The denture-securing device may advantageously secure dentures without requiring use of adhesives. The denture-securing device may also reduce the likelihood of food getting under dentures, provide a firm yet soft and comfortable fit, and minimize rocking of lower dentures. The denture-securing device may advantageously be secured to gums using a suction fit through saliva or other sources of moisture.

16 Claims, 7 Drawing Sheets

DENTURE-SECURING DEVICE

FIELD OF THE INVENTION

The invention relates to a denture-securing device. More particularly, the invention relates to a denture pad useful for securing dentures to human gums without the use of adhesives.

BACKGROUND

The irregularities of the contours of the upper and lower gums traditionally pose difficulties with fixing dentures in a position within a mouth. These difficulties are heightened as the contours of the gums may continually change as the mouth moves during normal use. Various solutions have been proposed to overcome these difficulties, but such solutions fail to provide a substantially secure attachment of dentures within the mouth as it may move during normal use. Examples of such incomplete solutions include use of powdered adhesives, viscous materials, and other undesirable adhesive products. As an additional disadvantage of using adhesive products, saliva may reduce the viscosity or adhesive properties of such products. This saliva containing adhesives may be accidentally swallowed leading to stomach irritation.

What is needed is a denture-securing device that may substantially secure dentures to gums. What is needed is a denture-securing device to substantially secure dentures within a mouth without requiring adhesives. What is needed is a cleanable and reusable denture-securing device for substantially securing dentures within a mouth. What is needed is a denture-securing device constructed using materials having a low likelihood of irritating the inside of the mouth or stomach and no association with causing serious health problems.

SUMMARY

A denture-securing device is described herein that substantially secure a dentures to a user's gum within a user's mouth without requiring adhesives. The denture-securing device is also secured to a denture. The denture-securing device is cleanable and reusable and can be constructed using materials having a low likelihood of irritating the inside of the mouth or stomach.

A denture-securing device is provided for substantially securing a denture within the mouth of a user. The denture-securing device may function as a pad and to reline and bond the denture to the gum of the user. The denture-securing device may be constructed using materials unlikely to cause irritation with the mouth or stomach and having a low likelihood of causing any health problems. Materials may include 100% wood pulp paper materials or in another embodiments, fabric or linen fibers. These materials may be folded a number of times, for example, 8 to 12 times, to increase absorption properties of water or saliva by the denture-securing device. The denture-securing device may be cleanable and reusable, allowing a saturation of cleaning solution by the pad as it is cleaned. The denture-securing device may be substantially zinc free.

The denture-securing device may be provided in multiple pieces, which may be applied to one or more dentures. For example, the denture-securing device may include a first pad and a second pad that can be placed on surfaces of the dentures that will interface with the gums to which the dentures will be installed. This use of multiple pads may be applicable to both upper and lower dentures. The pads may be trimmed to fit dentures of various sizes and shapes. In another embodiment, the denture-securing device may be constructed as a single unitary piece.

The denture-securing device may be constructed as a single pad or as two or more pads. In embodiments that include two pads, the first pad and second pad may each include a miter edge that adjoin one another at and fold over a front edge of the denture to provide secure attachment to the denture.

In one embodiment, supplements may be added to the denture-securing device to provide minerals or other contents to a user. For example, mastic drops may be administered or otherwise included by the denture-securing device for delivery to a user, such as via the gums.

Accordingly, the invention features a denture-securing device for securing a denture to a human gum. The denture-securing device includes at least one pad having multiple layers of material for placement on a denture that is affixable to a human gum. The at least one pad adheres to the human gum via suction when the at least one pad is moistened.

In another aspect, the invention can feature the at least one pad including a first pad installable on a first side of the denture and a second pad installable on a second side of the denture.

In another aspect, the invention can feature the first pad including a first pad miter edge and the second pad including a second pad miter edge. The first and second pads adjoin at their respective miter edges.

In another aspect, the invention can feature a front portion of the first pad miter edge and a front portion of the second pad miter edge fold at least partially over a front of the denture.

In another aspect, the invention can feature the multiple layers of material including at least two separate pieces of the material arranged in layers.

In another aspect, the invention can feature the multiple layers of material being a single piece of material folded so as to be configured into at least two layers.

In another aspect, the invention can feature the multiple layers of material including at least two separate pieces of material, wherein each separate piece of material is folded so as to be configured into at least two layers, and wherein the at least two separate piece of material are arranged in layers after folding.

In another aspect, the invention can feature the pad being constructed from wood pulp paper.

In another aspect, the invention can feature the pad being constructed from fabric, linen fibers, or a combination of the foregoing.

In another aspect, the invention can feature the pad being cleanable and reusable.

In another aspect, the invention can feature the at least one pad including mastic.

In another aspect, the invention can feature the at least one pad being placed into a channel of the denture before affixation to the human gum.

In another aspect, the invention can feature the at least one pad partially or entirely covering the channel of the denture.

In another aspect, the invention can feature the denture being an upper denture or a lower denture.

In another aspect, the invention can feature the at least one pad being moistened by saliva present in a user's mouth.

A method of the invention can be used for affixing a denture to a gum. The method includes the steps of: (a) placing at least one pad having multiple layers of material for placement on a denture; and (b) affixing the denture to a human gum by moistening the at least one pad.

Another method of the invention can include the step of installing the at least one pad into a channel of the denture.

Another method of the invention can include the step of moistening the at least one pad with saliva, water, or another suitable solution.

Another method of the invention can include the step of folding an edge of the at least one pad at least partially over a front of the denture to secure the at least one pad to the denture.

Another method of the invention can include the at least one pad including a first pad installable on a first side of the denture and a second pad installable on a second side of the denture. The first pad can include a first pad miter edge and the second pad can include a second pad miter edge. The first and second pads adjoin at their respective miter edges. A front portion of the first pad miter edge and a front portion of the second pad miter edge fold at least partially over a front of the denture. The method further includes the step of: folding the first pad miter edge and the second pad miter edge of the at least one pad at least partially over a front of the denture to secure the at least one pad to the denture.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides a denture-securing device usable to substantially secure dentures within a mouth. The denture-securing device may be used with top dentures, bottom dentures, or other configurations of dentures. The denture-securing device may advantageously secure dentures without requiring use of adhesives. The denture-securing device may also reduce the likelihood of food getting under dentures, provide a firm yet soft fit, and minimize rocking of lower dentures and partials. The denture-securing device may advantageously be secured to gums using a suction fit. The number of denture-securing devices required by a user is determined by the number of dentures the user wears in his or her mouth. For example, for a person having only an upper denture or only a lower denture, only one denture-securing device is needed. However, for a user who wears both upper and lower dentures, one denture-securing device is used to secure the upper denture to an upper gum in the user's mouth and a second denture-securing device is used to secure the lower denture to a lower gum in the user's mouth.

Figure 1:
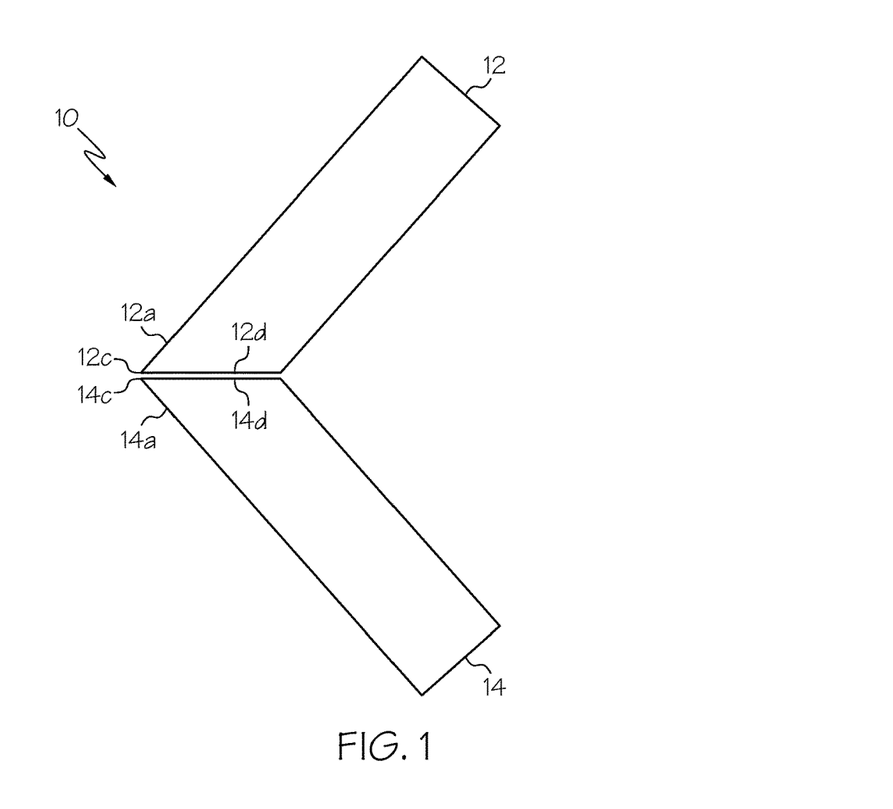
FIG. 1 is a top plan view of the denture-securing device according to an embodiment of the present invention wherein the denture-securing device includes a first pad and a second pad.
Figure 2:
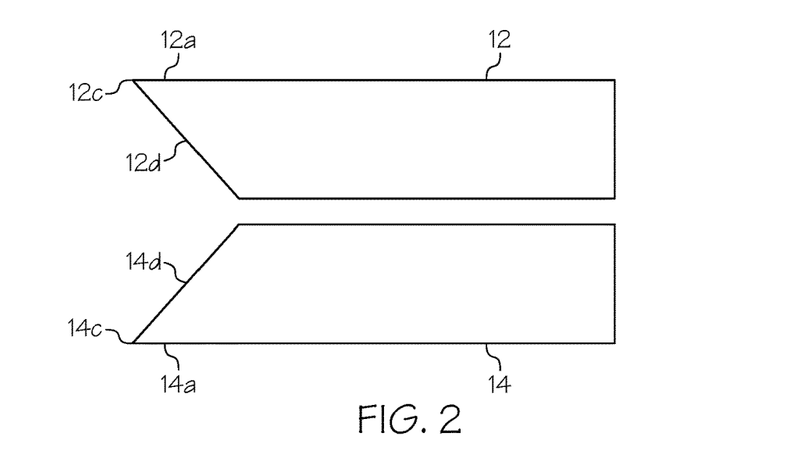
FIG. 2 is another top plan view of the first pad and second pad of the denture-securing device of FIG. 1.
Figure 3:
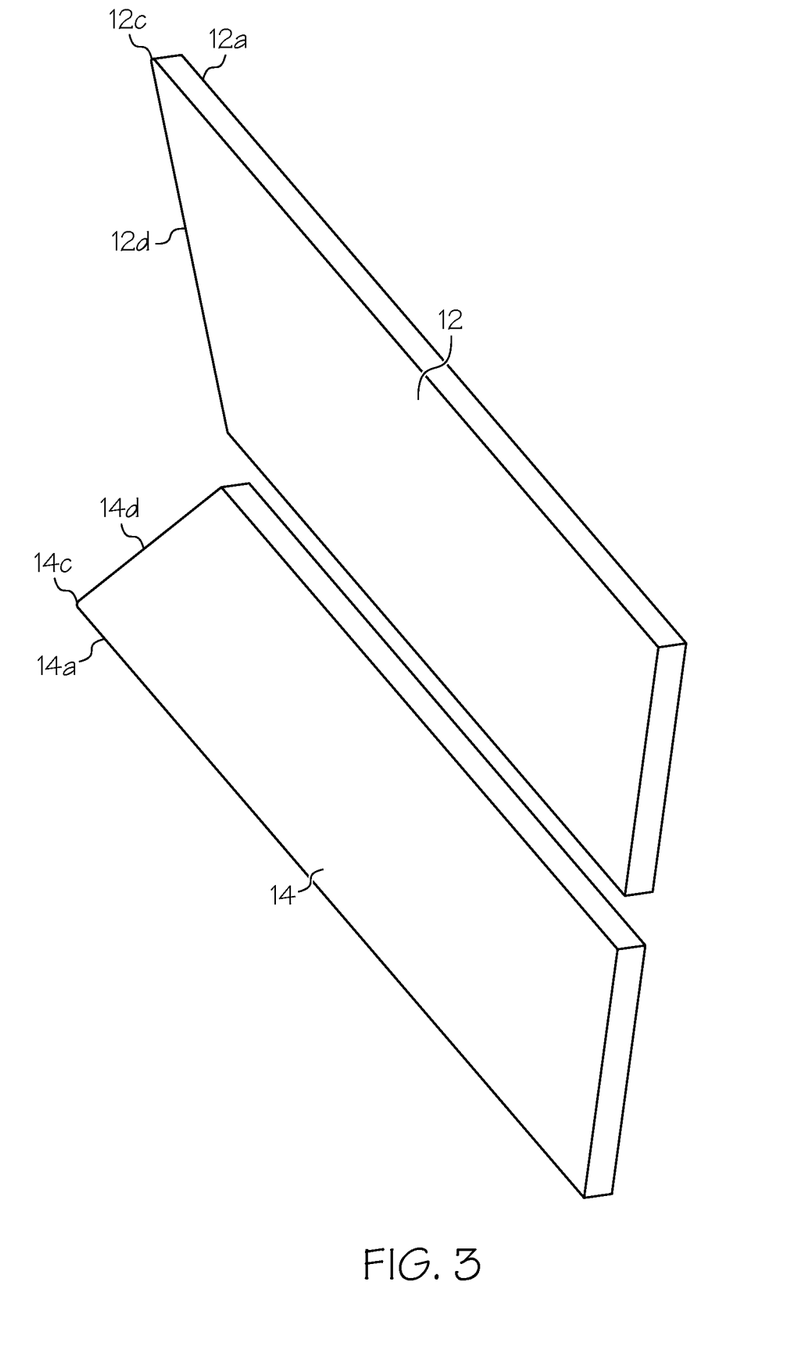
FIG. 3 is a perspective view of the first pad and second pad of the denture-securing device of FIG. 1.

Referring now to FIGS. 1-2, the denture-securing device 10 will be discussed in more detail. The denture-securing device 10 may function as a pad and also serves to reline and bond a denture. The denture-securing device 10 may be constructed using a folded piece of material that is formed into a pad 10. For example, the pad may be constructed using a folded paper product. In one embodiment, the folded paper product may be 100% wood pulp paper material. The material may be folded a number of times to achieve the desired thickness and other properties. In one example, the material may be folded between about 8-12 times. Skilled artisans will appreciate the material may also be folded, stacked, and/or placed one on top of the other, 1, 2, 3, 4, 5, 6, 7, 8, 9, 10, 11, 12, 13, 14, 15, 16, 17, 18, 19, 20, or more times, without limitation. In one embodiment, a single piece of material can be folded one or more times to create the pad 10. In another embodiment, two or more pieces of material may each be folded one or more times and layered one upon another to form the pad. In still another embodiment, one or more unfolded pieces of material and one or more pieces of material that have been folded one or more times may be layered one upon another to form the pad. In yet another embodiment, two or more unfolded pieces of material are layered one upon another to form the pad. In another embodiment, a single unfolded piece of material forms the pad. In at least one embodiment, the denture-securing device is constructed without using cotton.

Folding the denture-securing device is advantageous over using a puffy napkin configuration, as the folded denture-securing device provides for better water absorption, smaller and flatter form, improved fit around the gums, and reduced undesired expansion caused by absorption typical to traditional puffy napkins. The material may be a fabric material, such as a paper fabric material. In an alternative embodiment, the material may include polyester as a spun lace or non-spun lace. The material of the denture-securing device may be absorbent of water, saliva, and other liquids. Preferably, the material used to construct the denture-securing device is substantially zinc-free.

The denture-securing device may be cleanable. More particularly, the denture-securing device may be separable from the dentures and cleanable between applications for reuse. In one example, the denture-securing device may be separated from a denture when a user removes his or her dentures before going to sleep. In another example, the denture-securing device may be separated from the dentures after a user eats. The denture-securing device may be cleaned using water, denture cleaning tablets, and other cleaning products that would be appreciated by a skilled artisan. The denture-securing device may be at least partially submerged in water or another cleaning product as the denture-securing device is cleaned. For example, the denture-securing device may be cleaned in a denture back along with the dentures to which it may be installed, allowing for saturation during cleaning. Once the denture-securing device has been cleaned, it may be removably installed in the denture and reused.

Saliva in the user's mouth moistens the denture-securing device so that when it is installed in a channel of a denture and secured to a gum of the user in the user's mouth, the saliva creates a suction between the denture-securing device and the user's gum.

A liquid may be applied to the denture-securing device prior to installation and/or locating the dentures in the mouth. This liquid may advantageously reduce an undesirable dry mouth condition that may otherwise be experienced by some users. The liquid may include water, saliva, saline, or other liquids that would be appreciated by a skilled artisan. Additionally, supplemental ingredients may be added to the denture-securing device to add or alter the device. For example, mastic drops may be added to the denture-securing device so that a user may receive minerals upon placing dentures with the denture-securing device in his or her mouth. The mastic drops may be derived from mastic gum, such as an herb mastic gum. An antibacterial composition may optionally be included by the denture-securing device.

In another example, moisture may be added to the denture-securing device to improve hydration in the mouth of the user. The denture-securing device may be pre-soaked in its packaging, which may at least partially moisten the pad with water or another fluid to advantageously reduce reliance on saliva of the user to create suction to install the denture to the gums. A presoaked embodiment of the denture-securing device may be especially desirable to remedy dry mouth conditions that may otherwise be present in some users.

The denture-securing device may be constructed using a fibrous paper material, which may share similar properties with a moist towelette. The surface of the denture-securing device may be generally smooth. The denture-securing device may create its own suction, eliminating the need of suction pads or recesses.

In one embodiment of this disclosure, the denture-securing device may be configured as a single pad shaped to fit within a denture. In another embodiment of this disclosure, the denture-securing device may be configured as multiple pads, for example a first pad and a second pad. The first pad and second pad may have the same or similar dimensions. However, skilled artisans will appreciate that the first pad, second pad, and any other pads may have dimensions that differ from one another.

Figure 4A:
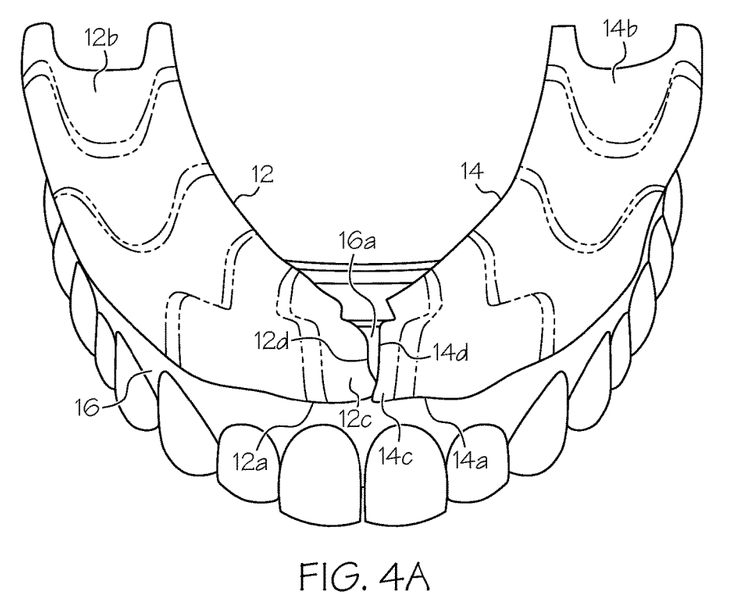
FIG. 4A is a front perspective view of the first pad and second pad of the denture-securing device of FIG. 1 installed on an upper denture.
Figure 4B:
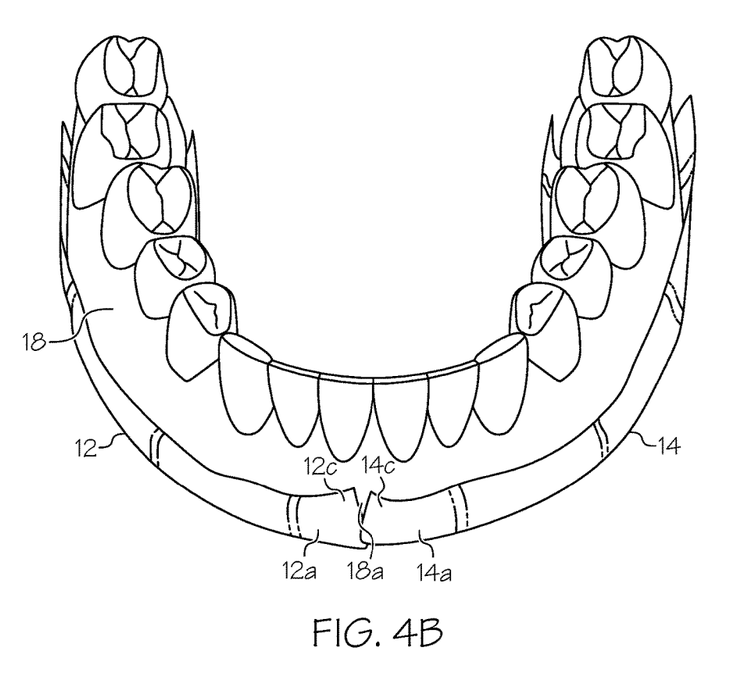
FIG. 4B is a front perspective view of the first pad and second pad of the denture-securing device of FIG. 1 installed on a lower denture.
Figure 5A:
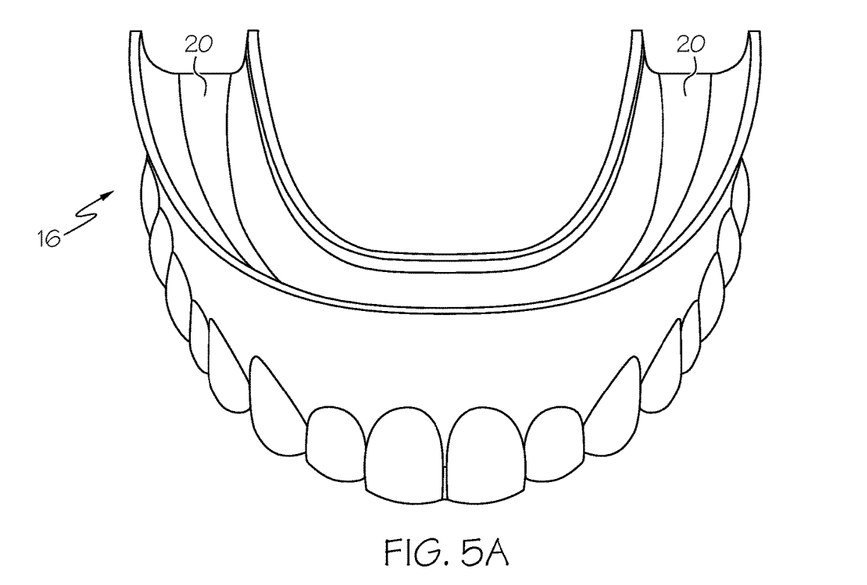
FIG. 5A is a front perspective view of the upper denture of FIG. 4A without the first pad and second pad of the denture-securing device installed thereon.
Figure 5B:
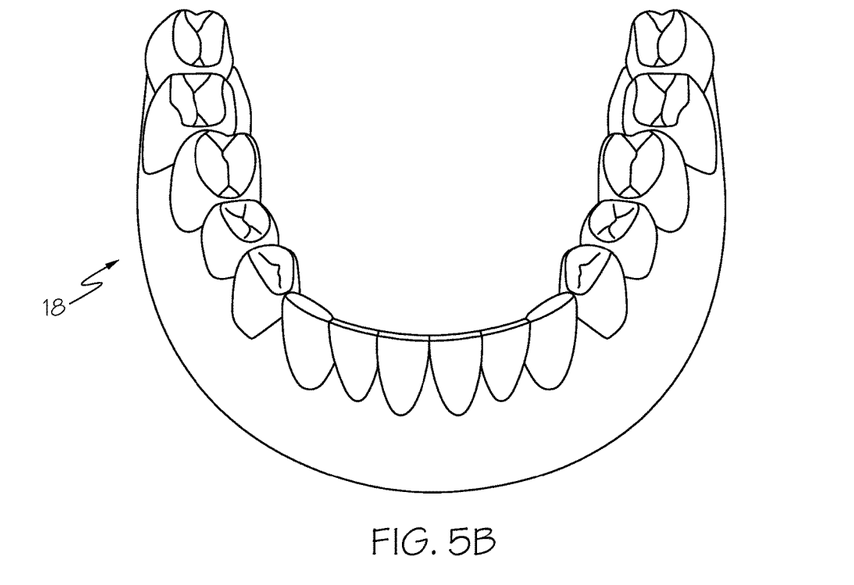
FIG. 5B is a front perspective view of the lower denture of FIG. 4B without the first pad and second pad of the denture-securing device installed thereon.
Figure 6:
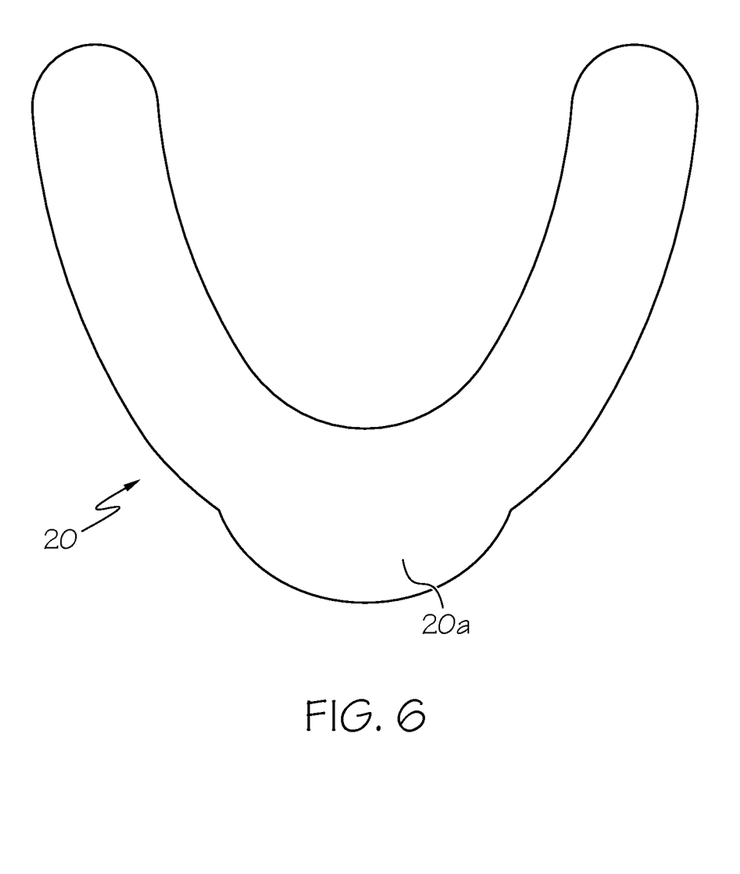
FIG. 6 is a top plan view of an embodiment of a denture-securing device constructed as a single unitary pad.
Figure 7A:
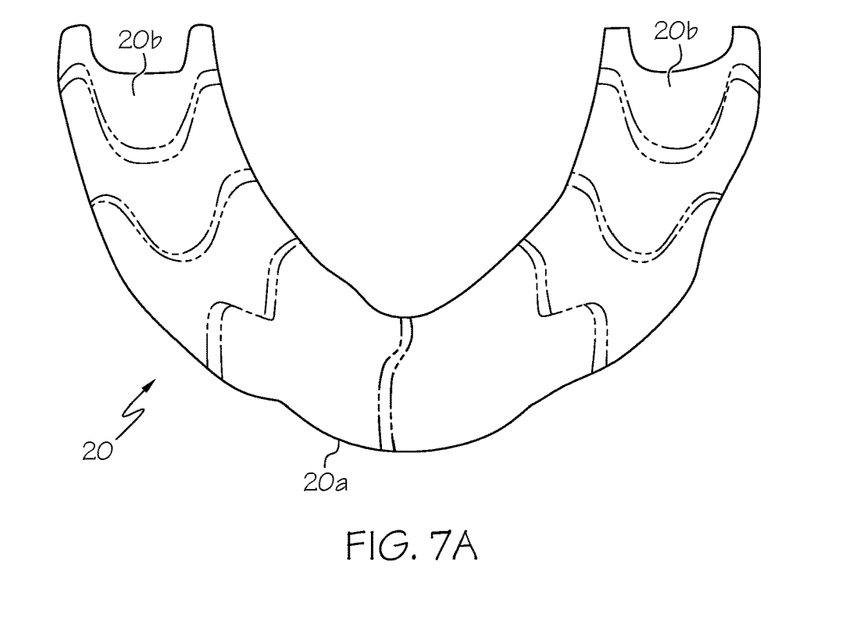
FIG. 7A is a top perspective view of the denture-securing device of FIG. 6, wherein the denture-securing device is shaped to correspond to the denture channel of an upper denture.
Figure 7B:
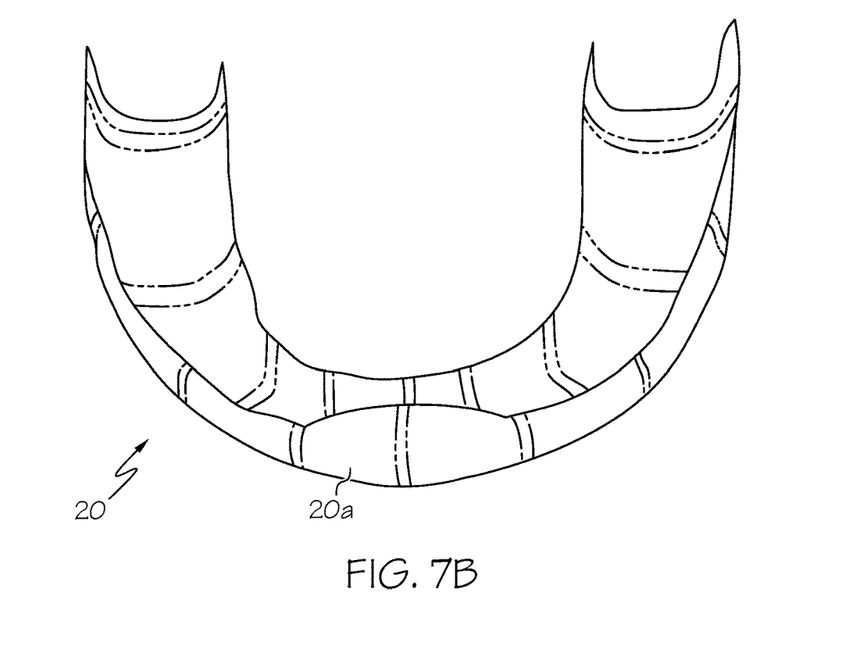
FIG. 7B is a top perspective view of the denture-securing device of FIG. 6, wherein the denture-securing device is shaped to correspond to the denture channel of a lower denture.

Referring to FIGS. 1-4B, an illustrative embodiment including two pads will be discussed. FIG. 1 illustrates a first pad 12 and a second pad 14 of the denture-securing device 10 in a substantially flat configuration. As shown in FIGS. 1 and 2, a first end 12a of the first pad 12 may be positioned near a first end 14a of the second pad 14. As illustrated in FIG. 4A, the first pad 12 and the second pad 14 of a denture-securing device 10 may be placed onto the gum-facing side of an upper denture 16. FIG. 4B shows the first pad 12 and the second pad 14 of a second denture-securing device 10 placed onto the gum-facing side of a lower denture 18. The first ends 12a, 14a of the first pad 12 and the second pad 14 may be placed so that the first ends 12a, 14a do not touch or partially overlap. The first pad 12 of the denture-securing device 10 may at least partially conform to the gum-facing surface of the denture 16 or 18 to which it is installed, creating a first pad channel 12b along the center of the denture channel 20 longitudinally to interface with the gum. Similarly, the second pad 14 of the denture-securing device 10 may at least partially conform to the gum-facing surface of the dentures, creating a second pad channel 14b along the center of the denture channel 20 longitudinally to interface with the gum. FIGS. 5A and 5B show upper and lower dentures, respectively, and the denture channel 20 of the upper denture is shown in FIG. 5A.

One or both of the first pad and the second pad can include a foldable front portion 12c, 14c, which are foldable over a front portion 16a, 18a of the denture 16 or 18 to which each pad is installed. The foldable front portion 12c of the first pad 12 and the foldable front portion 14c of the second pad each have a miter edge so that when installed to a denture, their arrangement (if not partially overlapping) is similar to a miter joint as shown in FIGS. 1 and 4A. The foldable front portions 12c, 14c of the first pad 12 and second pad 14 securely affix the denture-securing device 10 to the denture. By folding the foldable front portions over the front portion of the denture, the denture-securing device achieves a more secure attachment to the denture, without the use of adhesives, than conventional denture pads that are installed only within the denture channel of a denture and that do not include any portion that folds over the front portion of the denture.

Figure 8A:
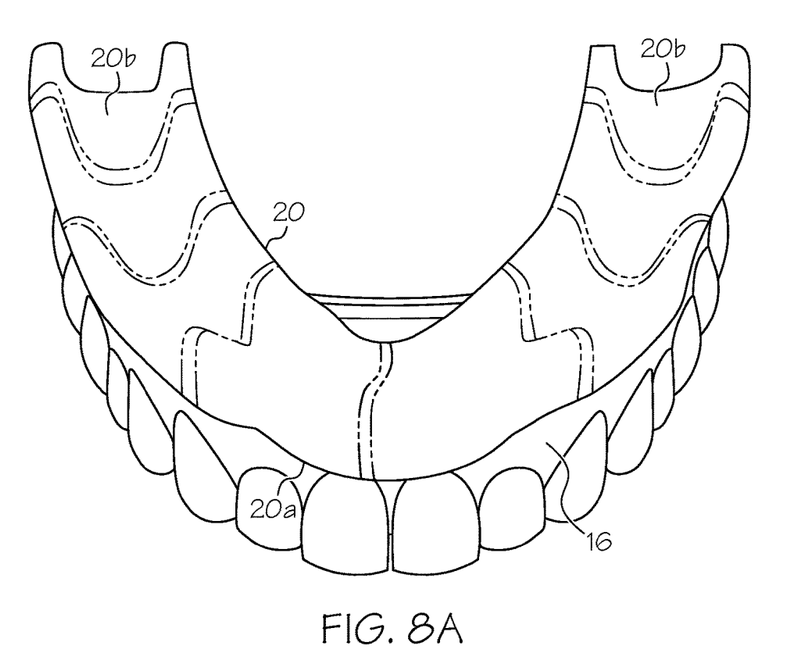
FIG. 8A is a top perspective view of the denture-securing device of FIG. 7A installed on an upper denture.
Figure 8B:
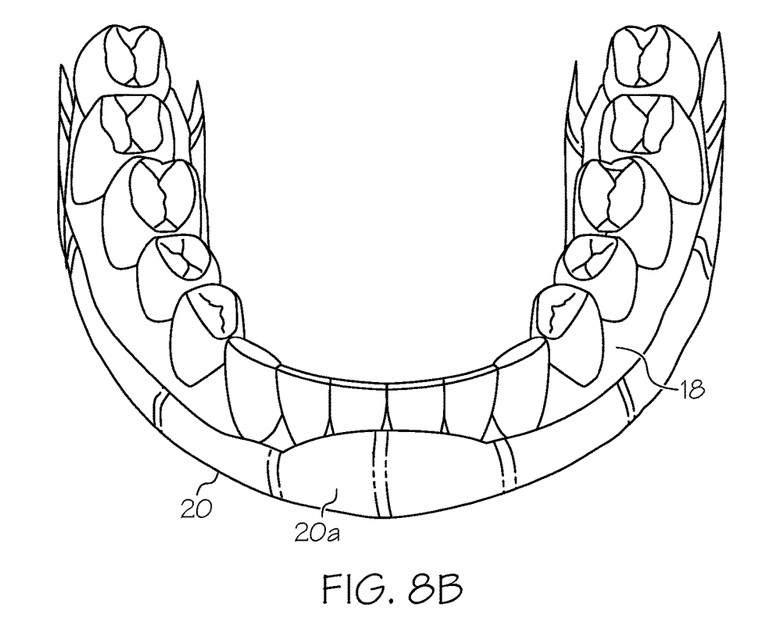
FIG. 8B is a top perspective view of the denture-securing device of FIG. 7B installed on a lower denture.

FIGS. 6-8B show an embodiment of the denture-securing device 20 that is constructed as a single unitary pad rather than as two or more pads. In FIGS. 7A and 7B, the single unitary pad 20 is shown formed into the shape the pad 20 takes when installed in a denture channel of an upper denture (in FIG. 7A) and in a denture channel of a lower denture (in FIG. 7B), e.g., while installed in the denture channel or after removal from a denture channel. The single unitary pad 20 forms a pad channel 20b when installed in (and after removal from) a denture channel. In FIG. 8A, the single unitary pad 20 is shown with a front edge 20a folded downward over a front portion of an upper denture 16 as it would be when securing the pad to the gum. In FIG. 8B, the single unitary pad 20 is shown with a front edge 20a folded upward over a front portion of a lower denture 18 as it would be when securing the pad to the gum.

As the dentures with the denture-securing device installed, which may include one or multiple pads, are compressed against the gums, the denture-securing device may create suction due to the presence of saliva or other moisture to substantially secure the dentures against the gums. The suction created may be sufficient to hold the dentures to the gums, but not so strong as to cause discomfort to the user.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A denture and denture-securing device assembly, comprising:
  a denture that is affixable to a human gum, the denture comprising a channel configured to receive a human gum with an outer edge and an outer side of the denture arranged outward of the human gum when the human gum is received within the channel; and
  a denture-securing device for securing the denture to the gum, the denture-securing device comprising at least one pad comprised of multiple layers of material for placement on the denture, wherein the at least one pad is absorbent; wherein
  the denture-securing device is mounted on the denture such that the at least one pad is placed into the channel of the denture, and such that a portion of the at least one pad folds over the outer edge of the denture and covers the outer side of the denture at least partially; and further wherein the at least one pad adheres to the human gum via suction when the at least one pad is moistened.

2. The denture and denture-securing device assembly of claim 1, wherein the at least one pad comprises a first pad installable on a first side of the denture and a second pad installable on a second side of the denture.

3. The denture and denture-securing device assembly of claim 2, wherein the first pad comprises a first pad miter edge and the second pad comprises a second pad miter edge, and wherein the first and second pads adjoin at their respective miter edges.

4. The denture and denture-securing device assembly of claim 3, wherein a front portion of the first pad miter edge and a front portion of the second pad miter edge fold at least partially over a front of the denture.

5. The denture and denture-securing device assembly of claim 1, wherein the multiple layers of material comprise at least two separate pieces of the material arranged in layers.

6. The denture and denture-securing device assembly of claim 1, wherein the multiple layers of material comprise a single piece of material folded so as to be configured into at least two layers.

7. The denture and denture-securing device assembly of claim 1, wherein the multiple layers of material comprise at least two separate pieces of material, wherein each separate piece of material is folded so as to be configured into at least two layers, and wherein the at least two separate piece of material are arranged in layers after folding.

8. The denture and denture-securing device assembly of claim 1, wherein the pad is constructed from wood pulp paper.

9. The denture and denture-securing device assembly of claim 1, wherein the pad is constructed from fabric, linen fibers, or a combination of the foregoing.

10. The denture and denture-securing device assembly of claim 1, wherein the pad is cleanable and reusable.

11. The denture and denture-securing device assembly of claim 1, wherein the at least one pad comprises mastic.

12. The denture and denture-securing device assembly of claim 1, wherein the at least one pad partially or entirely covers the channel of the denture.

13. The denture and denture-securing device assembly of claim 1, wherein the denture is an upper denture or a lower denture.

14. A method for affixing a denture to a gum, the method comprising the steps of:
   (a) obtaining a denture that is affixable to a human gum, the denture comprising a channel configured to receive a human gum with an outer edge and an outer side of the denture arranged outward of the human gum when the human gum is received within the channel;
   (b) obtaining a denture-securing device for securing the denture to a human gum, the denture-securing device comprising at least one pad comprised of multiple layers of material for placement on the denture, wherein the at least one pad is absorbent;
   (c) placing the denture-securing device on the denture such that the at least one pad is placed into the channel of the denture, and such that a portion of the at least one pad folds over the outer edge of the denture and covers the outer side of the denture at least partially to secure the at least one pad to the denture; and
   (d) affixing the denture to a human gum by inserting the human gum into the channel of the denture and moistening the at least one pad.

15. The method of claim 14, wherein step (d) further comprises the step of:
   moistening the at least one pad with saliva, water, or another suitable solution.

16. The method of claim 14, wherein the at least one pad comprises a first pad installable on a first side of the denture and a second pad installable on a second side of the denture;
   wherein the first pad comprises a first pad miter edge and the second pad comprises a second pad miter edge;
   wherein the first and second pads adjoin at their respective miter edges;
   wherein a front portion of the first pad miter edge and a front portion of the second pad miter edge fold at least partially over a front of the denture; and
   wherein the method further comprises the step of:
   folding the first pad miter edge and the second pad miter edge of the at least one pad at least partially over a front of the denture to secure the at least one pad to the denture.

* * * * *